United States Patent [19]

Athey et al.

[11] Patent Number: 5,481,018

[45] Date of Patent: Jan. 2, 1996

[54] AMINO NITRILE INTERMEDIATE FOR THE PREPARATION OF ALANINE DIACETIC ACID

[75] Inventors: Phillip S. Athey, Lake Jackson; David A. Wilson, Richwood; Druce K. Crump, Lake Jackson, all of Tex.

[73] Assignee: The Dow Chemical Company, Midland, Mich.

[21] Appl. No.: 414,606

[22] Filed: Mar. 31, 1995

[51] Int. Cl.$^6$ ................................................. C07C 255/28
[52] U.S. Cl. ........................................ 558/442; 562/571
[58] Field of Search ............................................... 558/442

[56] References Cited

U.S. PATENT DOCUMENTS

| | | | |
|---|---|---|---|
| 2,387,976 | 10/1945 | Bersworth | 260/534 |
| 2,407,645 | 9/1946 | Bersworth | 260/534 |
| 2,500,019 | 3/1950 | Bersworth | 260/534 |
| 2,538,024 | 1/1951 | McKinney et al. | 260/465 |
| 2,860,164 | 11/1958 | Kroll et al. | 260/534 |
| 2,867,654 | 1/1959 | Town | 260/518 |
| 3,061,628 | 10/1962 | Singer, Jr. et al. | 260/465.5 |
| 3,415,878 | 12/1968 | Gaunt | 260/534 |
| 3,429,915 | 2/1969 | Bersworth | 260/534 |
| 3,969,257 | 7/1976 | Murray | 252/102 |
| 4,120,800 | 10/1978 | Valcho et al. | 252/8.55 D |
| 4,801,742 | 1/1989 | Quirk et al. | 562/450 |
| 4,827,014 | 5/1989 | Baur et al. | 558/441 |
| 4,973,730 | 11/1990 | Baur et al. | 558/372 |
| 5,019,296 | 5/1991 | Baur et al. | 252/546 |
| 5,130,476 | 7/1992 | Baur et al. | 562/571 |
| 5,208,363 | 5/1993 | Crump et al. | 558/346 |
| 5,250,728 | 10/1993 | Parker et al. | 562/565 |
| 5,350,541 | 9/1994 | Michael et al. | 252/549 |
| 5,362,412 | 11/1994 | Hartman et al. | 252/94 |
| 5,380,452 | 1/1995 | Blanvalet et al. | 252/117 |

OTHER PUBLICATIONS

Mighri et al., Bulletin de la Société Chimique de France, (1975), pp. 1155–1159.

*Primary Examiner*—Joseph Paul Brust

[57] ABSTRACT

A novel intermediate useful in the synthesis of alpha-alanine diacetic acid or its salts is disclosed. The intermediate can be formed by contacting alanine with glycolonitrile under alkaline conditions or glycine with lactonitrile to form an aminonitrile which can be hydrolyzed and then contacted with additional glycolonitrile to form the nitrile intermediate which can be converted to alpha-alanine diacetic acid via hydrolysis.

1 Claim, No Drawings

AMINO NITRILE INTERMEDIATE FOR THE PREPARATION OF ALANINE DIACETIC ACID

BACKGROUND OF THE INVENTION

The present invention is to novel intermediates useful in the synthesis of alanine diacetic acid.

Chelants or chelating agents are compounds which form coordinate-covalent bonds with a metal ion to form chelates. Chelates are coordination compounds in which a central metal atom is bonded to two or more other atoms in at least one other molecule or ion, called a ligand, such that at least one heterocyclic ring is formed with the metal atom as part of each ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Some of these activities result in chelants entering the environment. For example, agricultural uses or detergent uses may result in measurable quantities of the chelants in water.

As chelants may enter the environment from various uses, it would be desirable to have chelants that would readily degrade after use. It would be particularly advantageous to have a chelant which is biodegradable, that is, susceptible to degradation by microbes which are generally naturally present in environments into which the chelants may be introduced.

Alpha alanine diacetic acid (ADA) has been recognized as a chelant for use in a variety of applications. For example, U.S. Pat. Nos. 3,969,257 and 4,120,800 disclose the use of ADA as a perborate stabilizer in laundry detergents and Japanese KOKAI 55-157695, published Dec. 8, 1980 discloses the use of ADA as a builder in detergent compositions to complex with metal ions to reduce the hardness, i.e., free metal ion content, of the water.

Conventional routes for the synthesis of ADA include reacting imidodiacetic acid with a 2-halo propionic acid or by treating alanine with a 2-haloacetic acid. A disadvantage of this route of synthesis is that a salt, such as sodium bromide or sodium chloride is produced. Removal of the produced salt requires relatively expensive procedures such as crystallization, or if carried along with ADA, can cause corrosion of equipment in which such ADA is used.

It would therefore be advantageous to have a novel composition of matter that is useful as an intermediate in the synthesis of ADA which allows ADA to be produced by an improved process in good yields and at high conversions without the formation of a salt that is difficult to remove or that is corrosive to equipment exposed to ADA containing such a salt.

SUMMARY OF THE INVENTION

The present invention provides a novel composition of matter useful as an intermediate in the synthesis of alpha ADA. Specifically, the novel intermediate is a compound represented by the formula

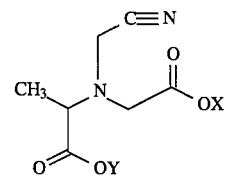

wherein X and Y each independently represent hydrogen, an alkali metal or alkaline earth metal.

In another aspect, the invention is to a process for producing ADA by basic hydrolysis of the above-noted intermediate.

The present invention also relates to hard surface cleaning compositions containing ADA in an aqueous system. The hard surface cleaning compositions provide a method for cleaning hard surfaces comprising contacting a hard surface with a composition containing alpha-alanine diacetic acid and removing a portion of the composition from the hard surface.

DETAILED DESCRIPTION OF THE INVENTION

As used herein, alanine diacetic acid, or ADA, means the alpha-alanine diacetic acid form of ADA. The convenient starting material for making the novel intermediate of the present invention can be alanine or glycine, including alkali and alkaline earth metal salts thereof. The isomeric form of the alanine used as starting material is not critical and commercially available d-, l- or dl-alanine can be used.

One suitable reaction scheme for the synthesis of an intermediate starting with alanine is shown in Scheme I. In step(a) alanine is contacted with glycolonitrile to form 2-(cyanomethylamino)propionic acid (I). The molar ratio of alanine to glycolonitrile is generally about 1:1 with a slight excess of glycolonitrile preferred.

Scheme I.

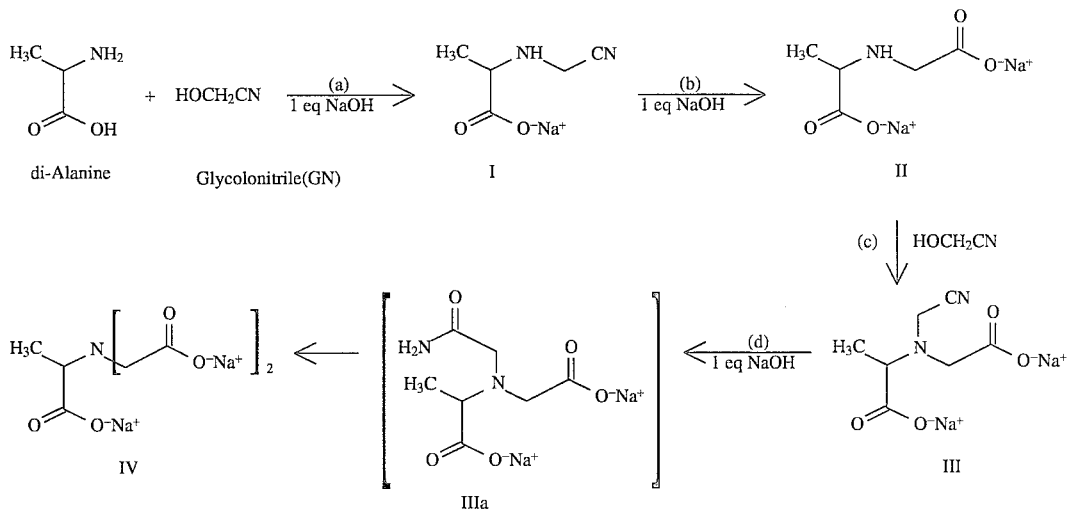

The hydrolysis of (I) with base gives 2-(carboxymethylamino)propionic acid (II). Compound (II) is then reacted with additional glycolonitrile to form N-(carboxymethyl)-N-(cyanomethyl)propionic acid (III). The molar ratio of (II) to glycolonitrile is generally about 1:1. In the above reactions, hydrogen cyanide and formaldehyde can be substituted for the glycolonitrile.

Compound (III) is useful as an intermediate for the production of ADA. Specifically, compound (III) is hydrolyzed using a base such as sodium hydroxide to give the alkali metal salt of ADA. Hydrolysis of the nitrile groups proceeds through the amide intermediate to the carboxymethyl group, as depicted by structure IIIa in Scheme 1, and liberates ammonia which can be conveniently removed from the hydrolysis solution.

In Scheme I, the reaction is shown as occurring in the presence of aqueous sodium hydroxide. The above reactions may be carried out in the presence of other bases capable of hydrolyzing the nitrile functionality. Examples of other bases include alkali and alkaline earth metal hydroxides. Preferably sodium or potassium hydroxide are used in the above reaction scheme.

In addition to bases, the nitrile functionality can be hydrolyzed using strong acids such as hydrochloric or sulfuric acid. In this case, the ammonium salt of the respective acid is obtained as a by-product.

While reaction Scheme I shows the addition of about one mole equivalent of base for the neutralization of alanine and about one mole equivalent per mole of nitrile functionality, excess molar amounts of base can be used.

Generally the glycolonitrile reaction steps (a) and (c) are carried out at a temperature of from about 0° to about 100° C., preferably from about 15° to about 65° C. The hydrolysis of (I) and (III) is generally done at a temperature from about 0 to about 120° C. Preferably the hydrolysis step (d) is done at a temperature from about 20° to about 105° C.

The hydrolysis of (III) to ADA results in a conversion in excess of 85 percent. The overall conversion of alanine to ADA on a molar basis by using the intermediate (III) is generally in excess of 80 percent.

In place of alanine, glycine can be used to prepare intermediate (III). In this case glycine is reacted with lactonitrile as shown in (Scheme II) to give 2-(carboxymethylamino)propionitrile (V) which is then hydrolyzed to give intermediate (II). The isomeric form of lactonitrile is not critical and d-lactonitrile, l-lactonitrile or d,l-lactonitrile can be used. Intermediate (II) can then be reacted with glycolonitrile to give the novel intermediate (III) which can be hydrolyzed to ADA. In the above reaction, acetaldehyde and formaldehyde can be used to replace lactonitrile. Preferably the lactonitrile reaction is carried out at a temperature from about 0° to about 100° C., preferably from about 15° to about 65° C.

Scheme II.

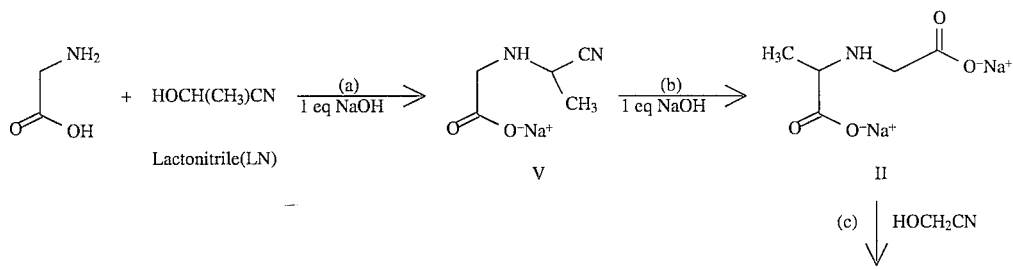

-continued
Scheme II.

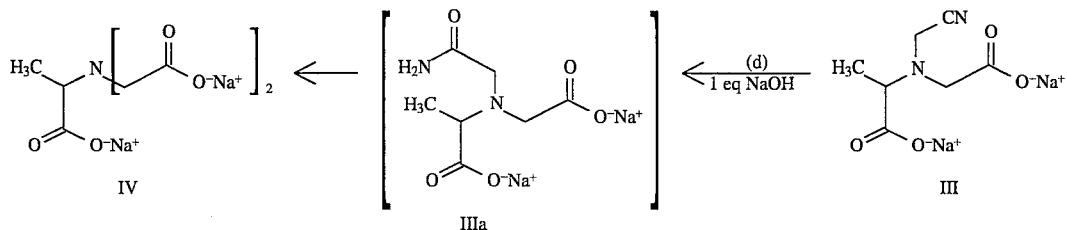

Although Scheme I indicates that the production of (III) and ADA are done in step reactions, the production of (IV) can be accomplished by adding glycolonitrile to an alkaline solution of alanine at temperatures necessary to achieve hydrolysis. In this case, intermediate (III) is rapidly converted to (IV) and (II). Species (II) is then converted to (IV) via intermediate (III) by the addition of additional glycolonitrile and caustic (Scheme III). As shown in Scheme III, the stepwise process is modified by mixing 3 equivalents of caustic with dl-filanine prior to the addition of glycolonitrile. Glycolonitrile is then slowly added to the hot reaction mixture. Upon complete addition of the glycolonitrile, ADA (IV) and 2-(carboxymethylamino)propionic acid (II) are present. The reaction is driven to completion by adding an equivalent amount of glycolonitrile and caustic necessary to convert (II) to ADA (IV).

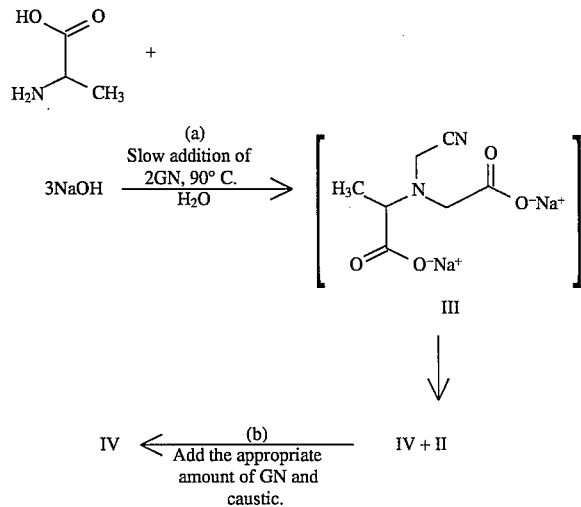

ADA is a chelant which will biodegrade in both the semi-continuous activated sludge test (ASTM D-2667) and the modified Sturm test (OECD 301B). In the activated sludge test, a standardized sludge containing municipal waste treatment plant organisms is used to biodegrade the chelant in the presence of metal ions representative of those found in the environment. Such a test simulates the environment encountered in a municipal waste treatment plant for screening the inherent biodegradability of non-volatile water-soluble compounds.

The modified Sturm test, in a similar manner contacts the chelant to a standardized culture of microorganisms. The evolution of carbon dioxide is used as a basis for determining microbial degradation when the test chelant is used as the sole carbon source.

ADA as a chelant is useful, for instance, in food products vulnerable to metalcatalyzed spoilage or discoloration; in cleaning and laundering products for removing metal ions, e.g. from hard water that may reduce the effectiveness, appearance, stability, rinsibility, bleaching effectiveness, germicidal effectiveness or other property of the cleaning agents; in personal care products like creams, lotions, deodorants and ointments to avoid metal-catalyzed oxidation and rancidity, turbidity, reduced shelf-like and the like; and in pulp and paper processing to enhance or maintain bleaching effectiveness. ADA can also be used in pipes, vessels, heat exchanges, evaporators, filters and the like to avoid or remove scale formation; in pharmaceuticals; in metal working; in textile preparation, desizing, scouring, bleaching, dyeing and the like; in agriculture as in chelated micronutrients or herbicides; in polymerization or stabilization of polymers; in photography, e.g. in developers or bleaches; and in the oil field such as for drilling, production, recovery, hydrogen sulfide abatement and the like. The amount of chelating agent employed in the above noted applications are known in the art.

The use of ADA is particularly advantageous for use in cleaning compositions suitable for hard-surface cleaning, such as certain automatic dishwashing agents and kitchen or bathroom soil removal, especially calcium soap removal from bathtub surfaces. ADA is particularly advantageous for use in hard-surface cleaners for use in control of alkaline-earth metals, particularly calcium, and in preventing scaling. When used in hard-surface cleaners, ADA generally constitutes at least about 0.1 weight percent of the cleaner and typically less than about 25%. Preferably the hard-surface cleaner contains about 0.1 to about 15 percent ADA, and more preferably about 0.5 to about 5 percent.

In addition to being biodegradable, it has been found that ADA can be used in hard-surface cleaners free of organic solvents. This is particularly advantageous in that cleaning can be done without the concern for release of organic solvent into the environment.

Hard-surface cleaning compositions containing ADA are usually at an alkaline pH with a range of about 8 to about 14. Preferably the pH of the cleaning composition is from about 9 to about 13, and more preferably from about 10 to about 12.

In addition to ADA, hard surface cleaners of the present invention can optionally contain additional additives well known in the art. For example, surface-active agents, are beneficial in a hard-surface cleaner.

Such surface active agents include water-soluble surfactants such as synthetic anionic, nonionic, cationic, amphoteric and zwitterionic surfactants and mixtures thereof. Exemplary surfactants include the alkyl benzene sulfates and sulfonates, paraffin sulfonates, olefin sulfonates, alkoxylated (especially ethoxylated) alcohols and alkyl phenols, amine oxides, sulfonates of fatty acids and of fatty acid esters, and the like, which are known in the detergency art. Preferably, such surfactants contain an alkyl group in about the C10–C18 range. Anionic surfactants are commonly used in the form of their sodium, potassium or triethanolammonium salts. The nonionics advantageously contain from about 3 to about 17 ethylene oxide groups per mole of hydrophobic moiety. Representative cationic surfactants include quaternary ammonium compounds such as ditallow dimethyl ammonium chloride, and are preferably used in combination with nonionic surfactants. Preferred in the compositions are about C12–C16 alkyl benzene sulfonates, about C12–C18 paraffin-sulfonates and the ethoxylated alcohols of the formula RO-(CH2-CH2O)n, with R being a C12–C15 alkyl chain and n being a number from 6 to 10, and the ethoxylated alcohol sulfates of formula RO-(CH2-CH2O)n-SO3M, with R being a C12–C18 alkyl chain, n is a number from about 2 to about 8, and M is H or an alkali metal ion.

Anionic surfactants are advantageously present at levels from about 0.3 percent to about 8 percent of the hard surface cleaning composition. Nonionic surfactants are preferably used at levels between about 0.1 percent to about 6 percent by weight of the composition. Mixtures of surfactants are also useful.

Other optional ingredients include detergent builders within the skill in the art, including nitrilotriacetate (NTA), polycarboxylates, citrates, water-soluble phosphates such as tri-polyphosphate and sodium ortho- and pyro-phosphates, silicates, ethylene diamine tetraacetate (EDTA), aminopolyphosphonates, phosphates and mixtures thereof.

Other optional additives for the hard surface cleaners include detergent hydrotropes. Exemplary hydrotropes include urea, monoethanolamine, diethanolamine, triethanolamine and the sodium potassium, ammonium and alkanol ammonium salts of xylene-, toluene-, ethylbenzene- and isopropyl-benzene sulfonates.

The hard-surface cleaning compositions of the invention also optionally contain an abrasive material. The abrasive materials include water-insoluble, non-gritty materials known for their relatively mild abrasive properties. It is preferred that the abrasives used herein not be undesirably "scratchy". Abrasive materials having a Mohs hardness of no more than about 7 are preferred; while abrasives having a Mohs hardness no more than about 3, are useful to avoid scratches on finishes such as aluminum or stainless steel. Suitable abrasives include inorganic materials, especially such materials as calcium carbonate and diatomaceous earth, as well as materials such as Fuller's earth, magnesium carbonate, China clay, actapulgite, calcium hydroxyapatite, calcium orthophosphate, dolomite and the like. The aforesaid inorganic materials can be described as "strong abrasives". Organic abrasives such as urea-formaldehyde, methyl methacrylate melamine-formaldehyde resins, polyethylene spheres and polyvinylchloride are advantageously used to avoid scratching on certain more delicate surfaces, such as plastic surfaces. Preferred abrasives have a particle size range of about 10–1000 microns and are preferably used at concentrations of about 5 percent to about 30 weight percent of the hard surface cleaning compositions.

Thickeners are preferably used to suspend the abrasives. Levels of thickener difficult to rinse from the cleaned surfaces are undesirable. Accordingly, the level is preferably less than about 2 percent, preferably from about 0.25 to about 1.5 percent. Exemplary thickeners include polyacrylates, xanthan gums, carboxymethyl celluloses, swellable smectite clay, and the like.

Soaps, especially soaps prepared from coconut oil fatty acids are also optionally included in the hard surface cleaners.

Optional components include components within the skill in the art to provide aesthetic or additional product performance benefits. Such components include perfumes, dyes, optical brighteners, soil suspending agents, detersive enzymes, gel-control agents, thickeners, freeze-thaw stabilizers, bactericides, preservatives, and the like.

The hard-surface cleaning compositions of the invention are advantageously in the form of liquid compositions, preferably aqueous compositions, including concentrates, containing as the essential ingredient ADA. Preferably a surfactant is also present, more preferably in a concentration that corresponds to from about 2 to about 6 percent surfactant. Concentrated liquid compositions preferably contain from about 6 to about 10 percent surfactant.

Alternatively, the compositions herein are in the form of creamy scouring cleansers, preferably containing an abrasive material, surface-active agent, and ADA.

The cleaning compositions can be packaged in a container that comprises a means for creating a spray, e.g., a pump, aerosol propellant or spray valve. The composition can be thus conveniently applied to the surface to be cleaned by conventional means, such as wiping with a paper towel or cloth, without the need for rinsing.

All parts, percentages and ratios herein are by weight unless otherwise indicated.

The invention will be further clarified by a consideration of the following examples which are intended to be purely exemplary of the present invention.

EXAMPLES

Example 1

The stepwise procedure for the synthesis of ADA:

2-(cyanomethylamino)propionic acid (I): In a 150 mL beaker was placed 10 g (0.11 mol) of dl-alanine, 75 mL of water and a magnetic stir bar. The pH of the solution was then adjusted to 10.9 by the addition of 6.86 g of 50% NaOH. While the solution was stirring glycolonitirle (GN, 40% aqueous, 16.05 g, 0.11 mole) was added dropwise. After 30 min the pH had dropped to 10.3. The pH was raised to 10.6 and stirred for another 30 min. A $^{13}$C NMR indicated that the conversion to I was complete. The contents of the solution were carried on to the hydrolysis step without purification. $^{13}$C NMR (D$_2$O):δ 21.1, 37.5, 60.8, 121.6, 184.3 ppm.

2-(carboxymethylamino)propionic acid (II): To solution of the mononitrile alanine produced by the above procedure was added 8.96 g of 50% NaOH. The resulting solution was then heated to a gentle boil for 30 min. A $^{13}$C NMR indicated that the hydrolysis was complete. The diacid was carried on to the next step without further purification. $^{13}$C NMR (D$_2$O): δ 20.9, 53.3, 60.9, 181.4, 185.2 ppm.

N-(carboxymethyl)-N-(cyanomethyl)propionic acid (III): The pH of the mixed diacid solution prepared by the above procedure was lowered to 10.5 by the careful addition of 6N HCl. A second equivalent of GN was added to the solution over a 5 min period. The solution was then stirred at room temperature for 45 min. A $^{13}$C NMR indicated that the reaction was complete. The nitrile was carried on to the hydrolysis step without further purification. $^{13}$C NMR (D$_2$O): δ 18.9, 43.2, 58.1, 66.2, 120.0, 181.1,184.0 ppm.

Hydrolysis to Alanine diacetic acid (IV): To a solution of III was added an additional 1.5 eq of 50% NaOH. The solution was then stirred at room temperature for greater than 12 h. A $^{13}$C NMR indicated that ADA was present in approximately 85% yield. The balance of the solution consisted mostly of the mixed diacid. $^{13}$C NMR (D$_2$O): δ 16.4, 59.6, 66.1, 183.1, 185.6 ppm.

Example 2

Glycine (5 g, 0.067 mol) was dissolved in 50 ml of water and placed in a 150 mL beaker. The pH of the solution was adjusted to 10 by the dropwise addition of an aqueous caustic solution. Lactonitrile (5.3 g, 0.068 mol) was added dropwise to the glycine solution with stirring at an ambient temperature. During the reaction the pH of the solution was maintained at greater than 9.4 by the addition of caustic solution. A $^{13}$C NMR indicated that the reaction was complete for the synthesis of 2-(carboxymethylamino) propionitrile (V) within 30 min. The contents of the solution were carried on to a hydrolysis step without purification. $^{13}$C NMR (D$_2$O): δ 21.0, 47.3, 52.9, 124.1,180.7 ppm.

2-(carboxymethylamino)propionic acid (II): The resulting solution (V) was allowed to stir at room temperature at a pH of 11.0. The hydrolysis was monitored by 13C NMR. The hydrolysis was complete between 12–18 h. The $^{13}$C NMR was as reported for (II) in Example 1.

Example 3

Synthesis of Alanine Diacetic Acid from Glycolonitrile in a Batch:

A stainless steel 3 L beaker equipped with an overhead mechanical stirrer and an inlet tube for GN was charged with 217 g of dl-alanine (2.44 mole), 610 g of 50% NaOH (7.63 mole) and 500 mL of water. The solution was heated to 90° C. at which point the first equivalent of GN (348 g of a 40% solution) was pumped in over a 2.5 h period. Throughout the overall reaction additional water was added periodically to keep the solution level around 1–1.2 L. The solution was heated for an additional hour to ensure that all of the ammonia had been evaporated off. A second equivalent of GN (348 g of a 40% solution, 2.44 mole) was pumped in over a 3 h period. The reaction solution was then analyzed by $^{13}$C NMR which indicated that 25% of the mixed diacid II (Scheme I) was still present. Accordingly, an additional amount of NaOH was added (48.8 g of 50% caustic), followed by the slow addition of an additional amount of 40% GN (24.4 g, 0.61 mol).

Subsequent analysis of the reaction solution indicated that less than 5% of the mixed diacid II was present. The solution was heated an additional 12 h at 85°–90° C. to ensure complete hydrolysis of the intermediate amide to ADA. The overall yield of ADA was approximately 95%. The contents of the reaction vessel were weighed and bottled. The final weight of the solution was 1255 g. The theoretical weight of the trisodium salt of ADA was 661.51g. $^{13}$C NMR (D$_2$O): δ 16.3, 59.7, 66.2, 183.1, 185.6 ppm.

Example 4

The procedure of ASTM D2667 is used to determine the inherent biodegradablity of ADA (alpha-alanine diacetic acid, IV).

Copper titration value is used to measure the extent of biodegradation of the chelating agents during the procedure. Titration is performed using ammonium purpurate (indicator for complexometric titration commercially available from Aldrich Chemical Co., Inc. under the trade designation Murexide) as the indicator at approximately pH 8, and using sodium acetate as buffer. Titration of 2.1 mg alanine diacetic acid (0.0102 mMoles) in 100 mL water with 0.01 molar copper chloride gives an endpoint of 1.02 mL (1.07 mL total mL minus 0.05 mL blank, or 0.0102 mMoles), representing a 1:1 chelation of copper. Analyses are performed daily for a period of 28 days.

Results of the biodegradation screening are given in Table I:

TABLE I

| Compound | Time for greater than 80% loss of chelation |
| --- | --- |
| NTA (std.) | 3 days |
| EDTA (std.) | greater than 28 days |
| ADA | 3 days |

A control is used to verify the absence of interfering chelating substances in the test.

The results of the biodegradability test show that ADA (α-alanine diacetic acid) is inherently biodegradable and could be expected to be utilized by organisms in a municipal treatment facility after an acceptable acclimation period.

Example 5

The procedure of OECD 301B is used to determine the ready biodegradablity of α-alanine diacetic acid. OECD 301B Modified Sturm test is based on evolution of $CO_2$ as a basis for determining microbial degradation with the test compound as the sole carbon source.

Acclimated organisms from the ASTM-D2667 SCAS test are used as the seed innoculum. According to the procedure, a compound that produces 60% or greater of the theoretical amount of possible $CO_2$ within the 28-day test period passes the test and is considered to be readily biodegradable.

Results of the modified Sturm test are given in TABLE II:

TABLE II

| Compound | Amount of Theor. $CO_2$ Produced |
| --- | --- |
| ADA (IV) (α-alanine diacetic acid) | approximately 75% |
| acetic acid (standard) | approximately 80% |

These data demonstrate that ADA (α-alanine diacetic acid) is readily biodegradable according to the OECD 301B Modified Sturm test.

Example 6

Calcium chelation capacity of ADA

The applicability of ADA for use in hard surface cleaners, was measured by the calcium oxalate and calcium carbonate titrations.

For titration with calcium oxalate, between 1 to 2 millimoles of ADA is weighed in a 60 mL beaker. After the addition of 30 mL deionized water and 5 mL of a 3% ammonium oxalate solution, the pH is slowly adjusted to about 11.6 with 20% sodium hydroxide. The solution is titrated with 0.1M CaCl$_2$ to the first permanent turbidity. The chelation valve is then determined from the mL of titrant used based on the following calculation.

Chelation Value=(mL titrant used×molarity titrant)×100 mg $CaCO_3$ per mmole sample wt. in grams×activity of sample (as acid form)

The chelation value is the mg of $CaCO_3$ that can be chelated by one active gram of a chelant, such as ADA.

For carbonate titration, the above procedure is duplicated with 2 mL of 20% sodium carbonate solution replacing the use of the ammonium oxalate solution.

The turbidity produced in the carbonate titration is due to the formation of calcium carbonate, while the turbidity produced in the oxalate titration is due to calcium oxalate. Since calcium carbonate is more soluble than calcium oxalate (i.e., oxalate has a greater affinity for calcium than does carbonate), chelants often show a chelation value more near the theoretical 1:1 stoichiometry in a carbonate titration than in an oxalate titration. The results for the titration of ADA in the presence of oxalate and carbonate are given in Tables III and IV respectively.

TABLE III

| OXALATE TITRATION | | |
|---|---|---|
| Chelant | Chelation Value | Percent Theor. 1:1 |
| EDTA | 342 | 100 |
| ADA | 360 | approximately 74 |

TABLE IV

| CARBONATE TITRATION | | |
|---|---|---|
| Chelant | Chelation Value | Percent Theor. 1:1 |
| EDTA | 342 | 100 |
| ADA | 480 | approximately 98% |

The results from both the oxalate and carbonate titrations show that ADA exhibits a chelation value of equal to or greater than EDTA, depending on the indicator used. Therefore, for applications requiring calcium control, such as in hard surface cleaners, ADA can be used as a more biodegradable substitute for EDTA.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A compound represented by the following formula:

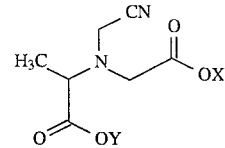

wherein X and Y are each independently hydrogen or an alkali metal or alkaline earth metal.

* * * * *